United States Patent [19]
Grooms et al.

[11] Patent Number: 5,918,821
[45] Date of Patent: Jul. 6, 1999

[54] MODULAR BONE GRINDER AND SNAP-IN GRINDER HEAD

[75] Inventors: Jamie M. Grooms, Gainesville; Kevin Carter, High Springs; Richard T. Schneider, Alachua, all of Fla.

[73] Assignee: G&G Technologies, Inc., Alachua, Fla.

[21] Appl. No.: 08/683,948

[22] Filed: Jul. 19, 1996

[51] Int. Cl.⁶ ................................................. B02C 19/12
[52] U.S. Cl. .......................... 241/27; 241/37.5; 241/100; 241/285.2
[58] Field of Search .................................. 241/100, 606, 241/37.5, 27, 285.2

[56] References Cited

U.S. PATENT DOCUMENTS

| | | | |
|---|---|---|---|
| 4,252,282 | 2/1981 | Vermeulen et al. | 241/236 |
| 4,706,897 | 11/1987 | Moeller | 241/37.5 |
| 4,884,755 | 12/1989 | Hedrington | 241/37.5 |
| 5,025,994 | 6/1991 | Maitlen et al. | 241/99 |
| 5,035,367 | 7/1991 | Nojima | 241/37.5 |

FOREIGN PATENT DOCUMENTS

| | | |
|---|---|---|
| 2199271 | 4/1974 | France . |
| 2712483 | 5/1995 | France . |
| 3808409 | 9/1989 | Germany . |

OTHER PUBLICATIONS

Albee, Fred H. (1940) Bone Graft Surgery In Disease, Injury And Deformity , D. Appleton–Century Company, Inc. pp. 1–31.

*Primary Examiner*—John M. Husar
*Attorney, Agent, or Firm*—Gerard H. Bencen, P.C.; Gerard H. Bencen, Esq.

[57] ABSTRACT

The bone grinder of this invention is capable of consistently producing ground bone particles of varying particle sizes, depending on the grinder head employed. The device provides the ability to easily interchange grinder heads according to the needs of a surgeon and the novel grinder head design optimizes the use of available bone stock by cutting the bone rather than crushing the bone.

27 Claims, 15 Drawing Sheets

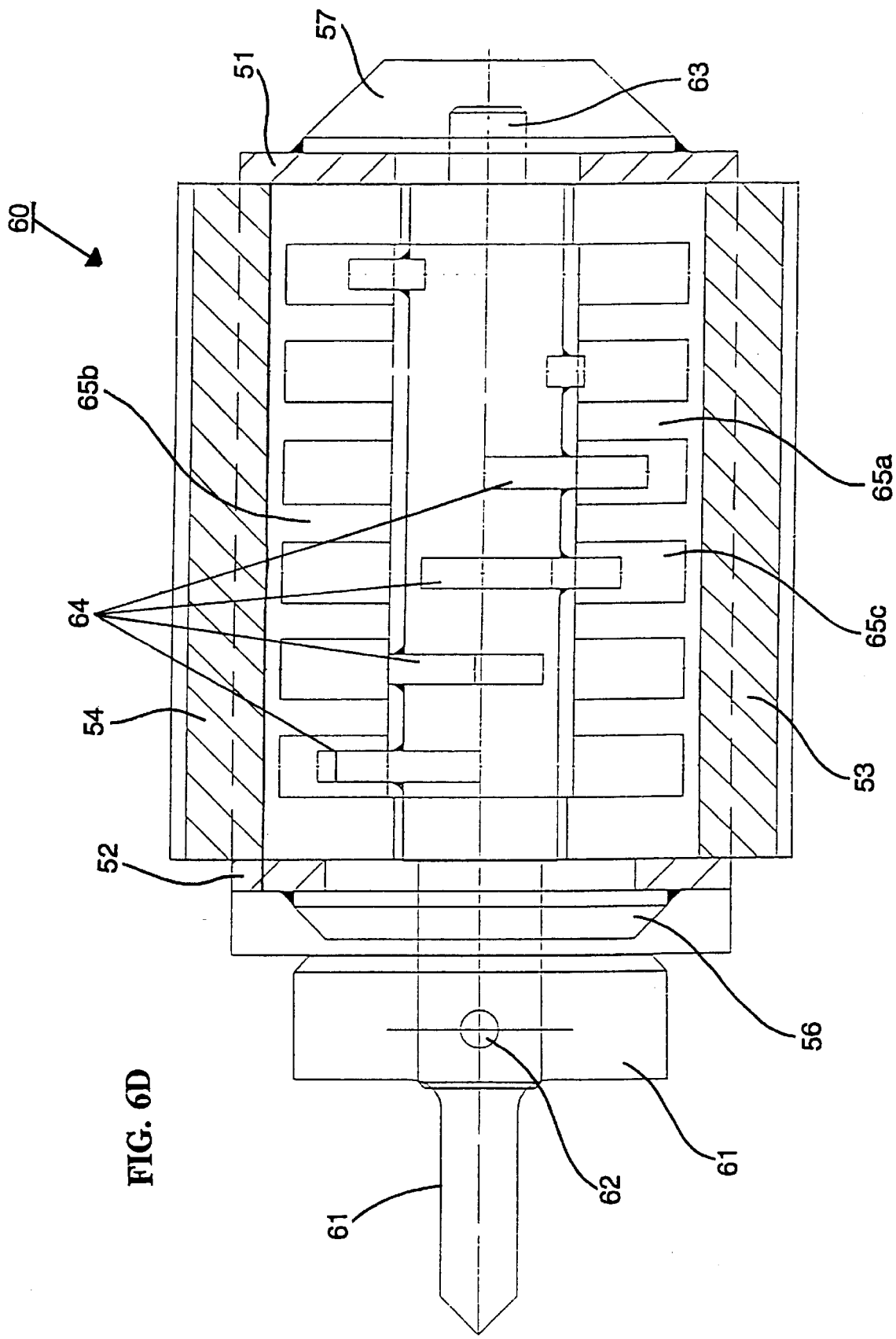

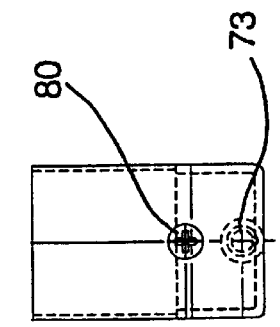
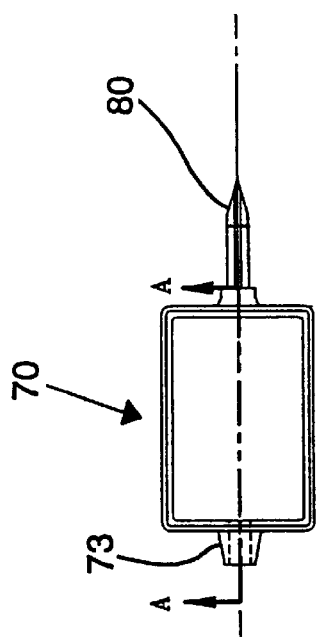
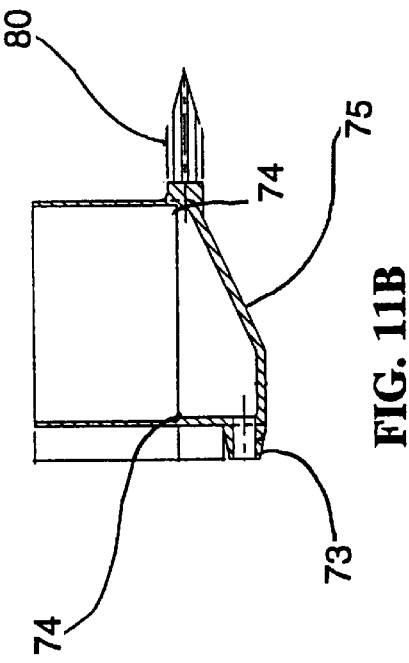
FIG. 11A
FIG. 11B
FIG. 11C

MODULAR BONE GRINDER AND SNAP-IN GRINDER HEAD

BACKGROUND OF THE INVENTION

I. Field of the Invention

This invention relates to a novel, modular, bone grinding apparatus, a method of using the apparatus and a method of making the apparatus. The bone grinder and ground bone product produced by this apparatus is superior in a number of respects to currently available ground-bone products.

II. Background

Grinding capabilities used in tissue banking and transplant surgery during the last two decades has been marginal. The types of grinders available did not produce variable particle sizes and shapes in an efficient, speedy and reproducible manner. Even one of the most popular grinders used today in the operating room is driven by a hand crank, which leaves a lot to be desired in terms of ease of use, safety, productivity and reproducibility of product. However, these distinctions aside, the use of known bone grinders in the operating room leaves much to be desired. They are not modular and do not allow for minimal disassembly for sterilization purposes and ease of sterile reassembly.

Ground bone is a product that is finding ever increasing use in the orthopaedic and other arts. Typically, ground bone is used to augment or repair defects in a recipient's bone during various types of implantation or other orthopaedic procedures. Production of this product is currently dependent on a number of machines, none of which fully meet the needs of the practicing orthopaedic surgeon, and none of which display the several advantageous features which comprise the device of the present invention. In particular, in reviewing the needs of surgeons and the exigencies of working with a living tissue such as a patient's own bone that needs to be ground in the operating room milieu, the available grinders are found to be wholly inadequate.

Examples of known devices can be found in DE 3808409, wherein a bone mill was disclosed which has a barrel-shaped grinding head which produces bone shavings. Unfortunately, such a grinding head is inefficient, and is only capable of producing a small amount of ground bone at a time of approximately one uniform particle size. In FR 2712483, there is likewise described a bone grinder which has a rotating grating cylinder, also capable only of producing ground bone of one approximately uniform particle size. In FR 2199271, there is described a grinding mill with a toothed rotor wherein two co-axial grinding wheels having conical surfaces grind material fed into the grinder. In U.S. Pat. No. 4,252,282, there is disclosed a "double-roll crusher" for crushing bones. However, a complete bone grinding apparatus for production of ground bone suitable for orthopaedic applications is not disclosed. Finally, it is known that certain bone mill manufacturing companies have produced bone grinding devices which, from the available product literature, appear to be quite similar to the DE 3808409 and FR 2712483 devices. Included in this group are the bone grinders produced by DePuy Inc., and Tracer Designs, Inc.

In the hands of the instant inventors, it has been found that available models of bone grinders have a number of unacceptable limitations, particularly when very scarce resources are available, such as when autologous bone is to be ground in an operating room setting for use in a patient whose own bone is to be ground and reimplemented in the course of surgery. For example, one known model employs a piston-driven, saw blade shaped grinder/cutting head. Frequent jamming of this device and metal fragmentation has been experienced. Continued hammering of the air-driven piston of the device by the operator's fist is required to produce the blasts of air to drive the saw blade.

In another known grinding device, available at the rather high cost of approximately $9,000.00, the grinding occurs by crushing and cutting by a hand crank driven grinding head. Typically, only rather muscular operators may use this device with success and the potential for binding, along with the overall large size of the grinder itself, make the device less than optimal for operating room settings. In addition, the device is only capable of producing bone particles of one size.

None of the known devices provide for a bone grinder having a modular grinder head that can easily be removed from a grinder and which can be separately sterilized, brought into the operating room, and snapped into place in an available grinder.

Accordingly, the present invention provides a novel bone grinding device which displays a series of advantageous features not found in the above published documents or in the known commercially available bone-grinding devices. This novel device better meets the demanding requirements of the operating room procedures which currently utilize inadequate grinder devices. This device likewise meets the high-volume needs of tissue banks worldwide for reproducible and efficient production of ground bone products.

BRIEF SUMMARY OF THE INVENTION

This invention is a novel bone grinder comprising a modular, snap-in and easily removable, and separately sterilizable grinder head which is capable of consistently producing ground bone particles of varying particle sizes depending on the grinder head employed. The device provides the ability to easily interchange grinder heads according to the needs of a surgeon and the novel grinder head design optimizes the use of available bone stock by cutting the bone rather than crushing the bone.

Accordingly, it is an object of this invention to provide a snap-in bone grinder head which can easily be sterilized and brought into surgery and snapped into an available grinder machine.

It is another object of this invention to provide a bone grinder capable of providing control over the particle size and type of bone used for any given surgical procedure.

It is another object of this invention to provide a bone grinder that can be used safely, efficiently and reproducibly in the operating room to grind autogenous bone so as to eliminate the need for use of allogeneic donor bone.

Another object of this invention is to provide a bone grinder capable of accepting a series of different bone grinding heads, each of which is capable of producing a consistent ground bone product that meets different orthopaedic needs.

Another object is to provide a series of novel bone grinding heads.

Another object is a means to water lavage ground product to remove undesirable compounds, i.e., blood cells or debris.

Another object of this invention is to provide a bone grinding system which includes a sterilized, disposable surgical tray for receipt of ground bone such that from procedure to procedure, the entire surface with which the bone comes into contact is completely sterilized and cross contamination between the bone ground by the instrument in each procedure is minimized or eliminated, so that autologous living bone tissue can be safely reimplanted.

Another object of this invention is to provide a single bone grinder capable of producing a series of different ground bone particle sizes.

Another object is to produce a bone grinder that minimally binds and which may easily be unbound by reversing the direction of grinder head rotation.

Another object is to provide a bone grinder capable of producing reproducibly sized particles of autologous and allogenic bone mixtures when supplemental bone is needed.

Another object is to provide a new bone cutter mechanism that cuts rather than crushes bone.

Another object is to provide a novel clutch means for insertion of a modular, snap-in grinder head into a grinder machine.

BRIEF SUMMARY OF THE FIGURES

FIG. 6D is a section through the grinder head.

FIGS. 11A–11C are schematics of the receiver cup.

DETAILED DESCRIPTION OF THE INVENTION

Figure 1:
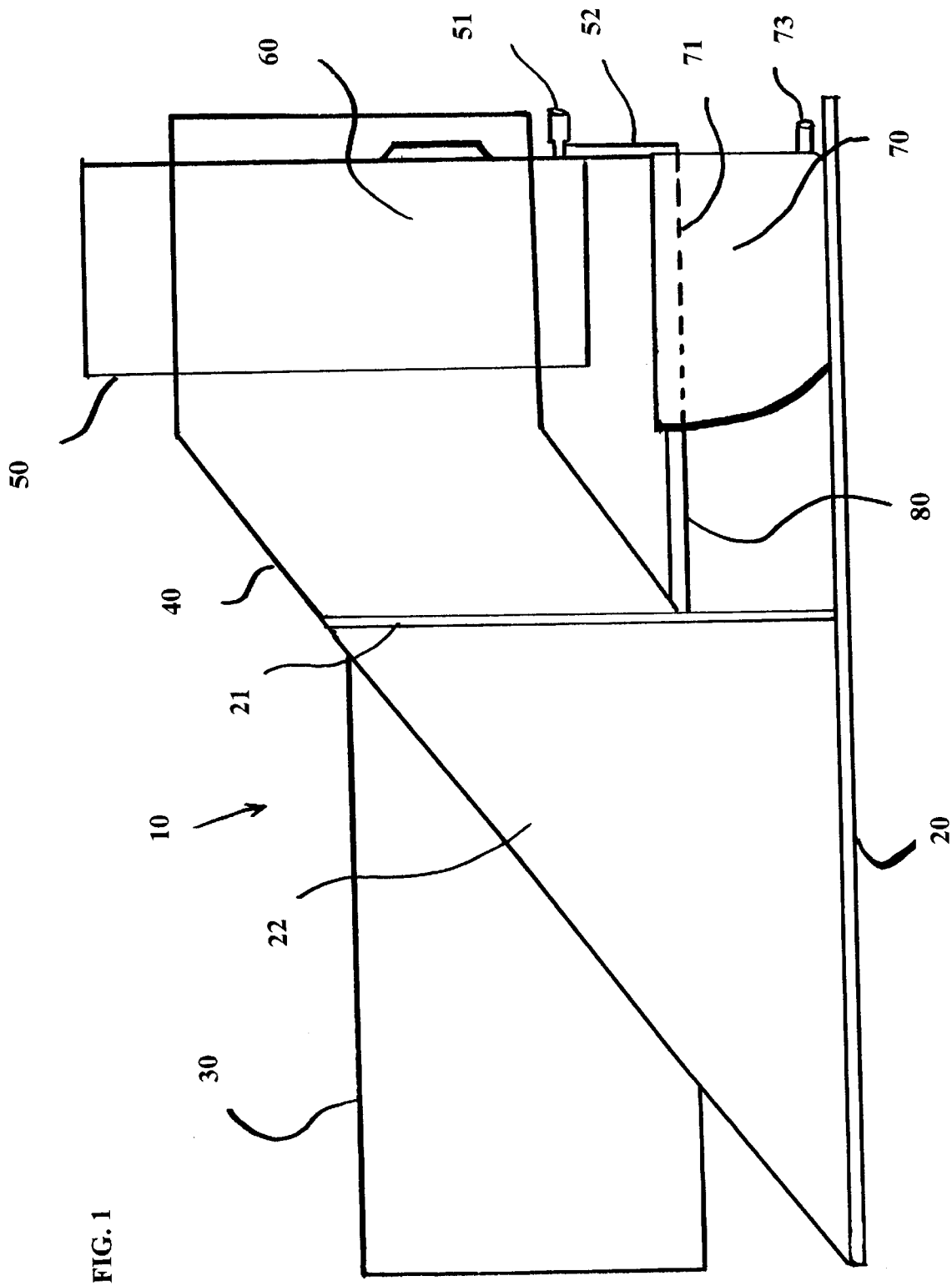
FIG. 1 is a side view schematic of the grinder of this invention showing the principal components of the device.

The grinder of this invention allows for easy and efficient set-up and customization of the grinding capability so as to produce various bone particle sizes and shapes, whether of cortical or cancellous bone. The grinder may be used to grind autogenous bone during a surgical procedure or may be used to regrind available allogeneic bone to desired particle sizes. In addition, the grinder may be used to grind and blend a combination of autogenous and allogeneic bone to create an homogenous mixture of uniform particle size in readiness for implantation.

Key features of the grinder that contribute to the ease of its setup and use include pre-packaged, sterile and disposable supply trays, interchangeable grinding heads which easily and smoothly glide into and out of the grinder and which can be sterilized prior to each use. The provision of a ground bone catch cup which allows for lavage of the ground bone allows for easy cleaning of the ground bone prior to use. Optional safety features, including a dual trigger device for motor activation, may be included to protect the grinder operator.

In order to fully appreciate the novelty and advantages of the device of this invention, it is necessary to consider some of the realities of the operating room setting where the use of this device is required. Currently, hand or circular saws are used which are cumbersome and potentially dangerous to operate. In addition, the existing grinders are not modular and thus are not amenable to sterilization of only portions of the device that come into contact with living tissue. In addition, not all working parts of existing bone grinders are resistant to harsh sterilization procedures, particularly where electrical torque development means (e.g. motors) form part of the device. Furthermore, since these devices tend to be rather heavy and bulky, it is impractical to have to lift and sterilize the entire device prior to each surgical procedure during which it might be necessary to grind autologous bone in a sterile field.

In the device of the present invention, a snap-in, modular grinder head is provided which can be easily removed from a grinder head housing. The grinder head housing may be thoroughly sterilized and maintained in a sterile field (e.g., under ultraviolet lights or by other means) while the modular grinder head may be snapped out of the housing and autoclaved, chemically sterilized or sterilized by other methods known in the art. The sterile grinder head, which is the only portion of the device which actually contacts the living autologous bone of a patient undergoing surgery, is then brought into the operating room fully sterilized. To optimize the ease of insertion of the grinder head into the grinder housing, the grinder head is provided with a novel clutch which allows insertion of the grinder head into the housing without the danger of contamination of the grinder head. Importantly, there is no need to use screws or other finicky elements to assemble the operative grinder device. Once the sterile grinder head of this invention is available, it is merely snapped into place and the device is ready to operate.

In addition to maintaining sterility of ground autologous bone by means of the aforedescribed modular grinder head, sterility is maintained by, in addition, providing a sterile drape and a sterile receiver cup where ground bone may be lavaged in situ.

Referring now to FIG. 1, there is provided a schematic of one embodiment 10 of the grinder of this invention. As can be seen from this figure, the device 10 comprises a base plate 20, a motor 30, a housing 40, a chute 50, a grinder head 60, a receptor vessel 70, and a safety rod 80. The snap-in grinder head of this invention preferably comprises the entire chute 50 and grinder head 60 assembly, with all other elements being generally susceptible to reference as the housing therefor or as the whole device. The various dimensions of each of these elements may, naturally, be varied considerably, without departing from the principles of this invention. However, to provide a guide, dimensions for one specific embodiment are provided. The length of the grinder may be approximately 16 inches long, 6.5 inches wide and about 10.25 inches high. One embodiment of the entire device weighs approximately 43 pounds. The device is preferably factory assembled on a sturdy base 20 and is preferably easily transportable. The device may rest alone on any table surface or may be held down or in place by any common means known in the art, including by clamping the device or by bolting the base plate 20 to a permanent surface. The grinder head 60 is driven by any of a number of known torque-producing means including, but not limited to, motor means, including an electric motor or, if there is concern about the possibility of igniting volatiles, by compressed air motors known in the art. In one embodiment, the motor may be a 0.25 horse power Bodine electric motor, or like motor.

Optionally, a foot pedal is provided to trigger easy and safe operation of the motor. Preferably, the base plate 20, housing 40, chute 50, and grinder head 60 are constructed from a durable material capable of sustaining the considerable forces needed to grind bone and repeated autoclaving or chemical sterilization procedures. One preferred material for construction of these elements is electro-polished #304 stainless steel which is heli-arc welded. Titanium is another desirable material that may be used for these purposes. Construction methods and materials known in the art may be used, but must provide for consistent performance, long life, reliability and durability.

Figure 2:
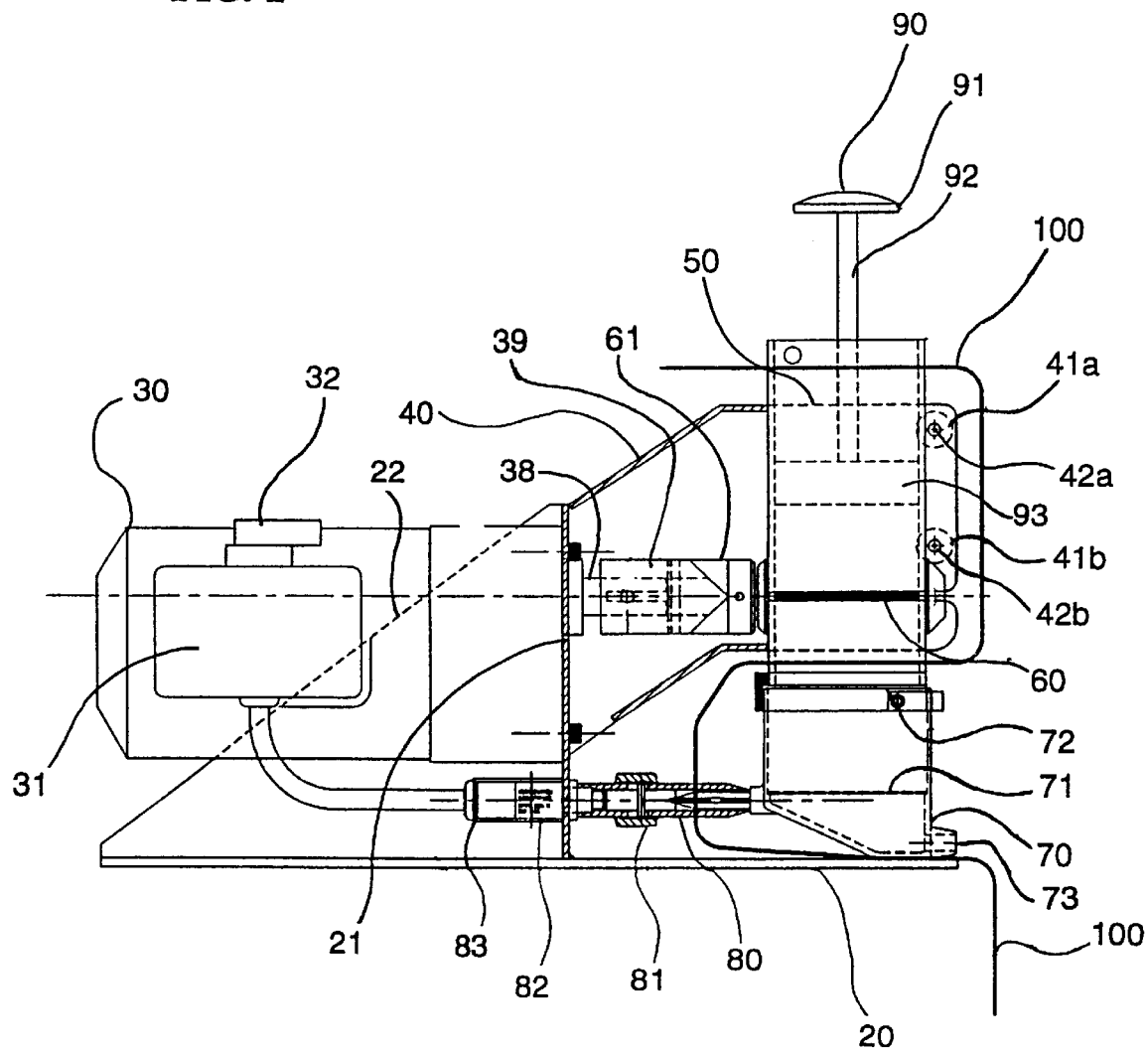
FIG. 2 is a detailed cross section of the embodiment of the grinder shown in FIG. 1.

Referring now to FIG. 2, there is provided a greater level of detail of the various features and components of the grinder shown in outline in FIG. 1. This figure shows the base plate or weldment 20, to which there is welded a vertical wall 21, and the housing 40. The motor 30 is mounted on the vertical wall 21 and may be enclosed in rearward projections 22 of the vertical wall which may also be welded to the base plate 20. The vertical wall and rearward projection will aid in isolating the motor from the grinder head and thereby contribute toward maintenance of a sterile grinder field. Also shown are the chute 50 through which bone material to be ground is fed. The bone material is forced into the grinder head 60 by any of a number of different pressure application means. In this figure, a plunger 90 having a handle 91 a shaft 92 and a plunger head 93 is shown as one preferred alternative. Preferably, the plunger 90 is made from an easily sterilizable material which can be sterilized at the same time as the grinder assembly 50 and 60. The front end of the housing 40 is shown with two holes 41*a* and 41*b* which receive lock pins 42*a* and 42*b*, such as ball lock pins such as those available from Avibank #BLC4B25S or from Reid #BLBS-035. These pins retain the chute 50 and grinder head 60 assembly in place during operation while allowing for easy removal of this assembly after use for cleanup and sterilization or for exchange of the grinder head. The forwardly projecting arms of the housing 43*a* and 43*b* are welded to the vertical wall 21 and form an enclosure or housing for the chute 50 which contains the grinder head 60.

Also shown in FIG. 2 is the receptor vessel 70 which can act as a wash cup for ground bone delivered through the grinder head 60. The wash cup preferably comprises a screen 71 and a lid 72. In one preferred embodiment, affixed to the rear of the wash cup 70 is the safety rod 80. With its sub-elements, the safety rod 80 acts as a safety interlock so that the grinder head may only be operated when the wash cup 70 is securely in place. The sub-elements of the safety rod 80 include an activator 81, a microswitch 82, and a switch cover 83. Only when the safety rod 80 affixed to the rear of the wash cup 70 is properly inserted into operational position does electrical or compressed air contact through the activator 81 and microswitch 82 allow the motor 30 to turn on and deliver torque to the grinder head 60. This is because the activator 81 is normally biased so as to allow no electrical or air contact through the microswitch 82. The wash cup is maintained in place, for example, by a retention latch 52 (see FIG. 1), affixed to the front of the chute 50 by a screw or like means 51. By tightening the latch 52, the activator 81 is sufficiently biased inward to activate the microswitch 82. The delivery of torque from the motor 30 to the grinder head 60 occurs through a unique grinder head coupling 61 (also referred to herein as a clutch) such that no prior alignment of the grinder head 60 is required upon insertion into its operational position. The way in which this is accomplished is discussed in greater detail hereinbelow.

As a desirable optional feature, shown in FIG. 2, there is provided a path for a sterile, disposable curtain 100 which may be threaded around the operative portions of the grinder to maintain sterility. By providing three holes appropriately apart, access to the entrance and exit of chute 50 and the safety interlock is maintained.

Figure 3:
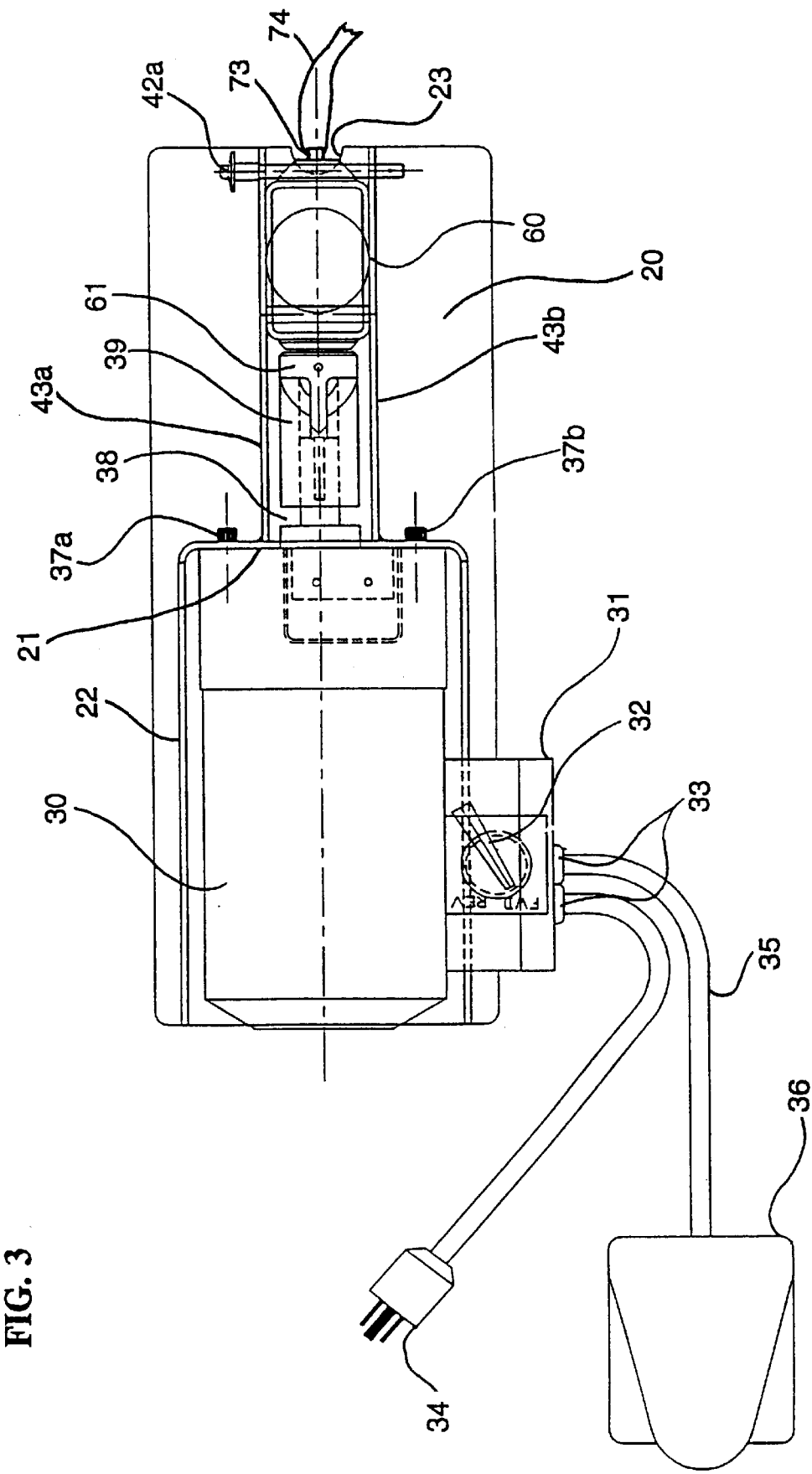
FIG. 3 is a top view of the embodiment of the grinder shown in FIG. 1.

Referring now to FIG. 3, there is shown a top view of the motor 30 along with the electrical sub-assembly and means of coupling the motor to the remainder of the grinder. The motor itself 30 may be any of a number of different torque generating means, including but not limited to an electrical motor, a hand crank, or a compressed air driven turbine. In one preferred embodiment, the motor 30 is a Bodine #42R5BFS1-E3 model #652, operating on 115 VAC, having a 20:1 ratio, operating at 85 rpm output speed, with ⅙ horse-power and reversible rotation. A junction box 31 is provided for isolating the electrical connections to prevent the possibility of ignition of volatiles in the operating room or elsewhere. A forward or reverse selection switch 32 is provided to allow selection of the direction (clockwise or counterclockwise) in which torque is to be applied. Grommets 33 are provided to seal the electrical cords as they enter the junction box 31. One electrical cord 34 acting as the power cord should be a grounded source of power. Optionally, another cord 35 is provided running to a foot operated pedal 36. Couplings 37*a* and 37*b* are provided to affix the motor 30 to the vertical wall 21 of the grinder. The motor output shaft 38 is affixed to a coupling 39 which couples with the coupling on the terminal end of the grinder head shaft 61. The grinder head 60 is shown in outline, and its retention in place by pin 42*a* is also shown. Aspiratory nipple 73 on the receiver cup 70, as well as an aspirator hose 74 are also evident. A semi-circular recess 23 in the base plate 20 accommodates the hose 74.

Figure 4:
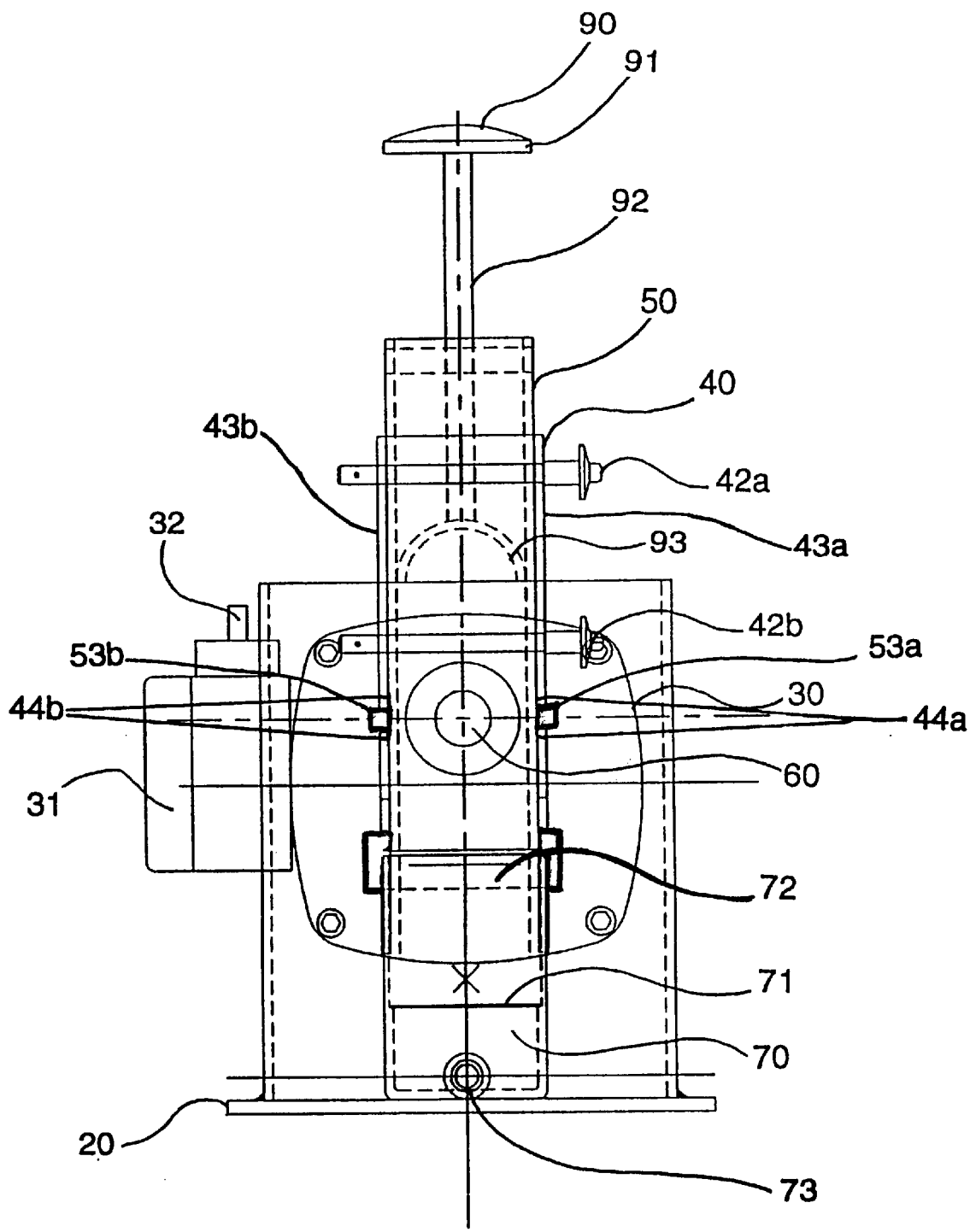
FIG. 4 is a frontal view of the embodiment of the grinder shown in FIG. 1.

Referring now to FIG. 4, there is shown a frontal view of the grinder, from the direction in which the removable elements of the grinder are removed or inserted into the housing 40. Like numbered elements in this figure correspond to the like numbered elements described above. From this figure, one begins to appreciate that, to disassemble the operative portions of this device, all that is required is removal of the lock-pins 42*a* and 42*b*. The chute 50 in which rides the grinder head 60 and the receiving cup 70 may all then easily be slid out of the grinder. The chute 50 slides on a pair of supports 53*a* and 53*b,* welded to the sides of the chute 50. While the shape of the chute is preferably square or rectangular, it will be recognized that other shapes may also be employed. The supports slide into slots 44*a* and 44*b* in sides 43*a* and 43*b* of the housing 40.

Figure 5:
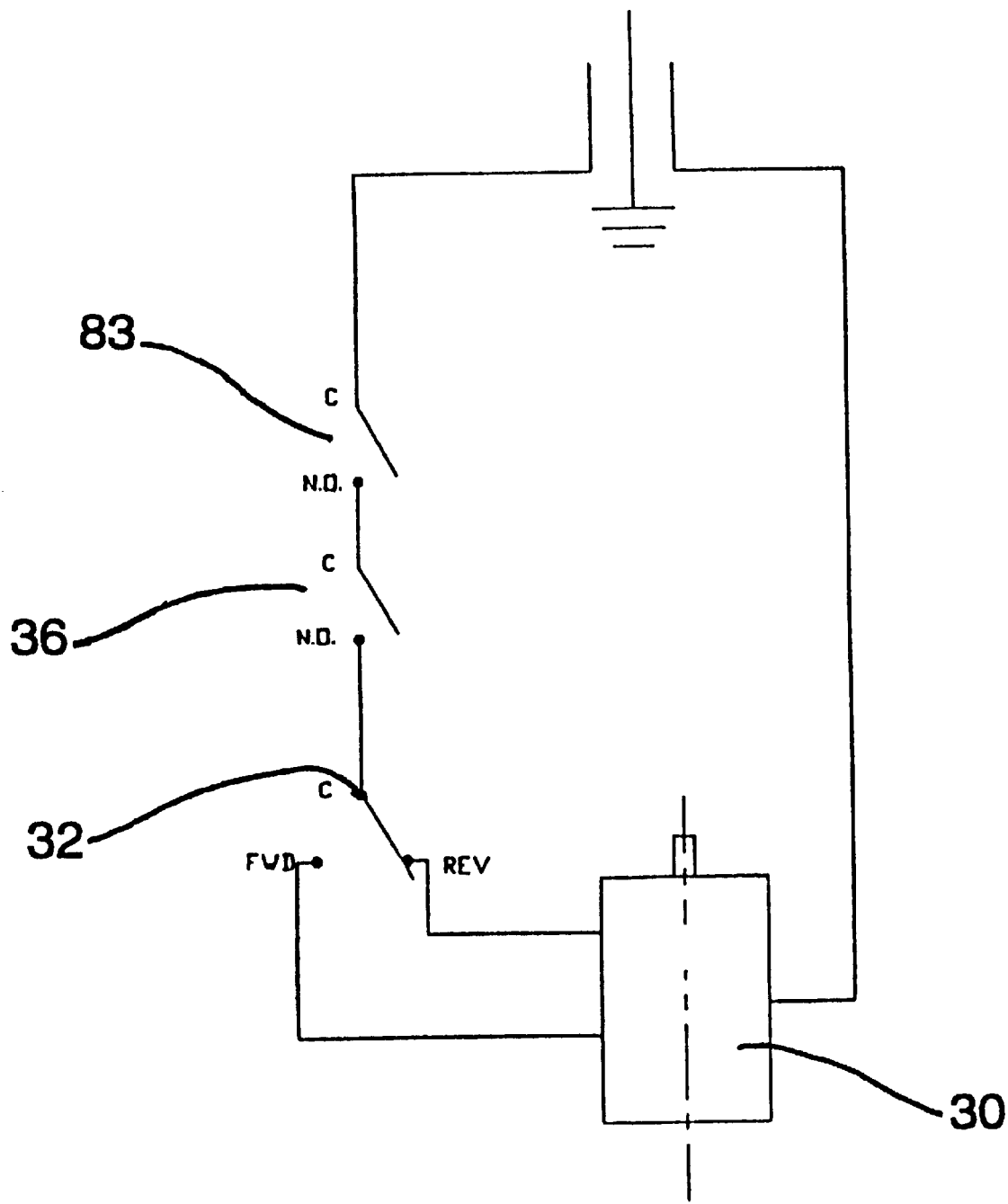
FIG. 5 is a simple wiring diagram of the embodiment of the grinder shown in FIG. 1.

In FIG. 5, there is provided a simple schematic of the electrical sub-assembly of the grinder, with previously numbered and described elements.

A series of different grinder heads 60 residing in chute 50 may be inserted into the grinder 10 of this invention. As will be appreciated, depending on differing dimensions of the grinder, the grinder head and chute 50 will be appropriately proportioned. To give specific examples, chutes of about 3 inches by 2 inches with a height of about 7 inches are appropriate. It is expected that the use of about three different grinding heads will meet the needs of between about 90 to 95% of the various orthopaedic and other procedures currently using ground bone. In addition, custom grinding heads, interchangeable with the three basic designs disclosed herein, could be prepared for use in the instant device. The features of the grinding heads 60 are described generally first, followed by a more detailed disclosure hereinbelow.

Each of the instant grinding heads preferably utilizes a "hook bill" shaped, staggered tooth configuration with beveled edges, which maximizes output of usable ground bone. Other tooth configurations could, however, be used without departing from the principles of this invention. The teeth and grinder head shaft are preferably made from a strong, durable metal, preferably #440C stainless steel to minimize wear at the grinding surfaces and to provide strength. As mentioned above, a stainless steel coupler connects the grind head shaft, also referred to herein as the cutter shaft, to the motor drive shaft. Overload protection is provided by a shear pin, and a reversible switch allows the user to prevent binding. The grinding head is fully sterilizable, by autoclaving or other means. Relatively large pieces of bone (for example a split femoral head) may be fed into the grinding mechanism while a plunger 90 is utilized to apply the desired downward pressure to cause the bone to remain in contact with the grinding head.

Figure 6A:
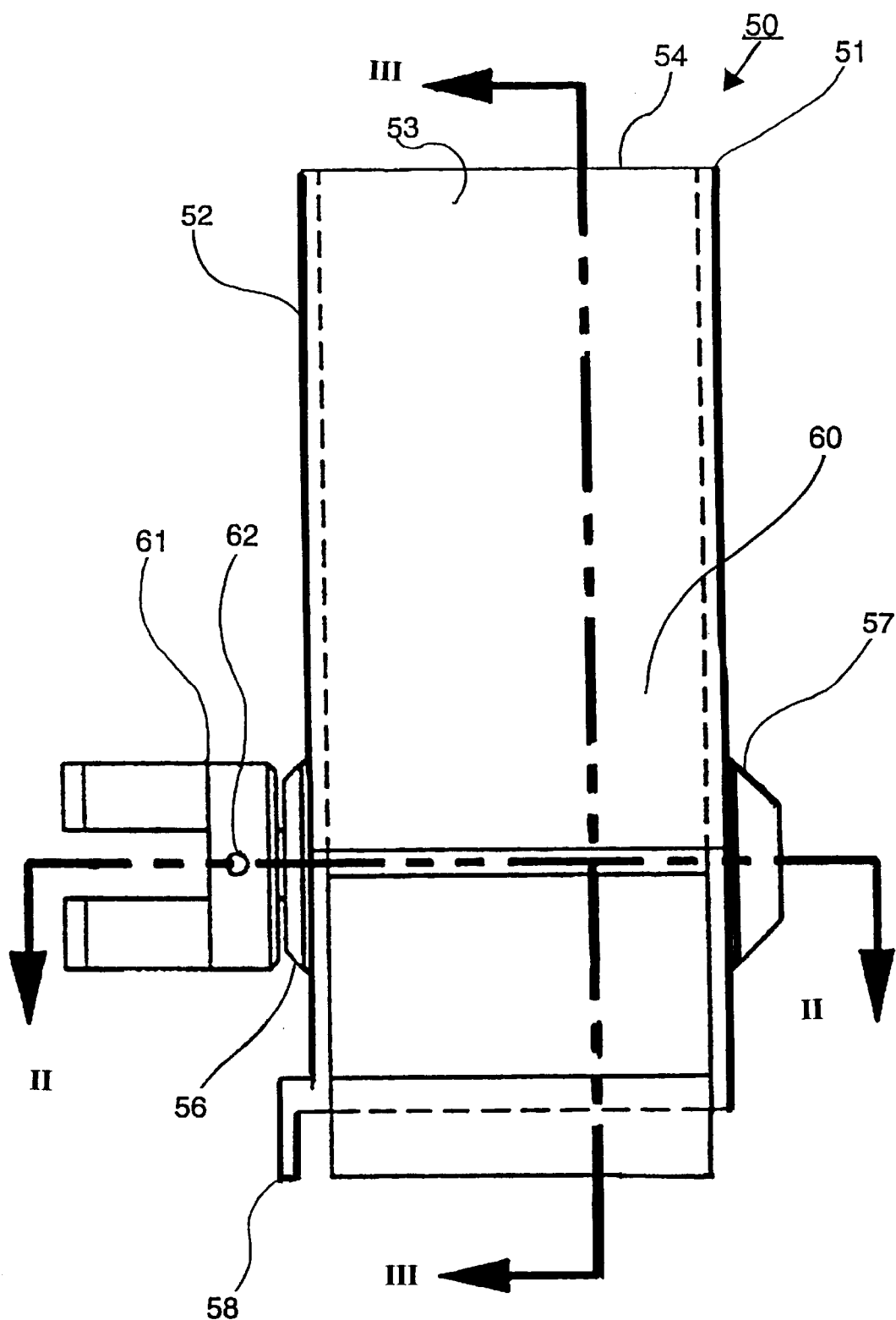
FIG. 6A is a side view of the grinder chute.

Referring now to FIGS. 6A through 6E, there are provided several views of the chute 50 and grinder head 60 assembly. In FIG. 6A, there is shown a side view of the chute 50 which comprises a front wall 51, a rear wall 52, and two side walls 53 and 54. A rear endcap 56 and a front endcap 57 are provided as protrusions in the rear 52 and front 51 walls respectively. These endcaps house the grinder shaft which rides on bearings mounted within the endcaps. Thus, in manufacturing the chute 50, the front wall, rear wall, and side walls are welded to form the chute, with holes remaining in the front and rear wall 51 and 52 to allow insertion of the assembled cutter head. The holes are then sealed by welding on the front and rear endcaps 56 and 57 with the cutter shaft firmly seated within the bearings seated in the front and rear endcaps. The rear endcap 56 has a hole of sufficient diameter to allow the cutter shaft to protrude and to affix the male coupling 61 thereto.

Prior to assembly of the welded chute, 50, a left wall half grate and right wall half grate are welded to the inside of the left and right walls. These half grate assemblies mesh with the cutter teeth (see below).

At the base of the rear wall 52, there is provided a rear guide plate 58. At the base of each side wall 53, 54, there is provided a side guide plate 59. Also shown in FIG. 6A is a portion of the grinder head 60 that emerges from the rear wall 52 of the chute 50. Evident are the grinder head coupling 61, along with a spring pin or set screw 62 which retains the grinder head coupling on the grinder head shaft (see below). The rear 58 and side 59 guide plates form a housing at the bottom of the chute 50 into which the receiver cup 70 fits.

Figure 6B:
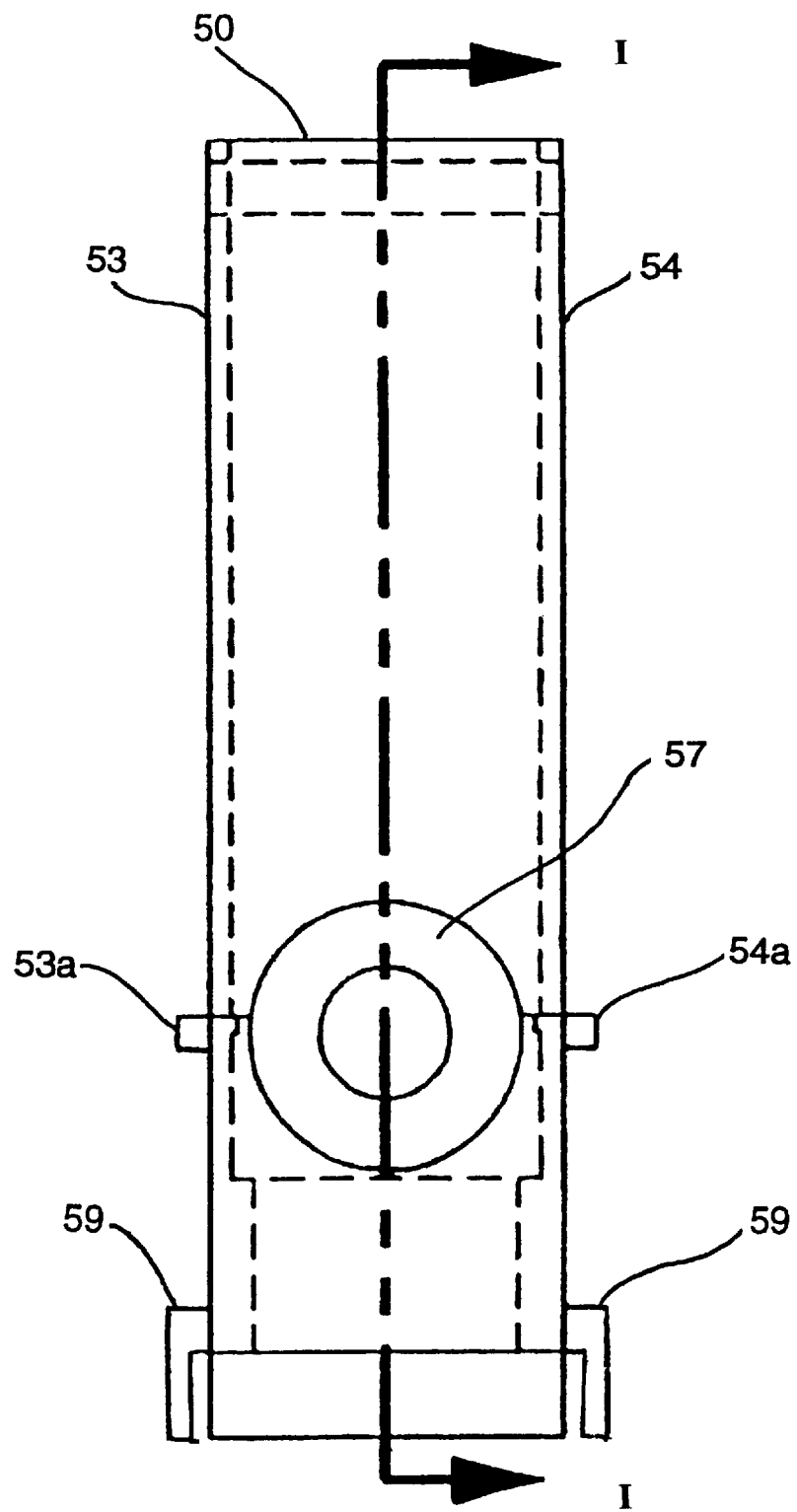
FIG. 6B is a frontal view of the grinder chute.

In FIG. 6B, there is shown a frontal view of the chute 50 assembly as it would appear to a user when the assembly is slid into the grinder 10. Elements with like numbering are described above. A pair of slide ridges 53a and 54a are provided respectively on the left 53 and right 54 side walls of the chute 50 which slide into the slots 44a and 44b in the housing 40.

Figure 6C:
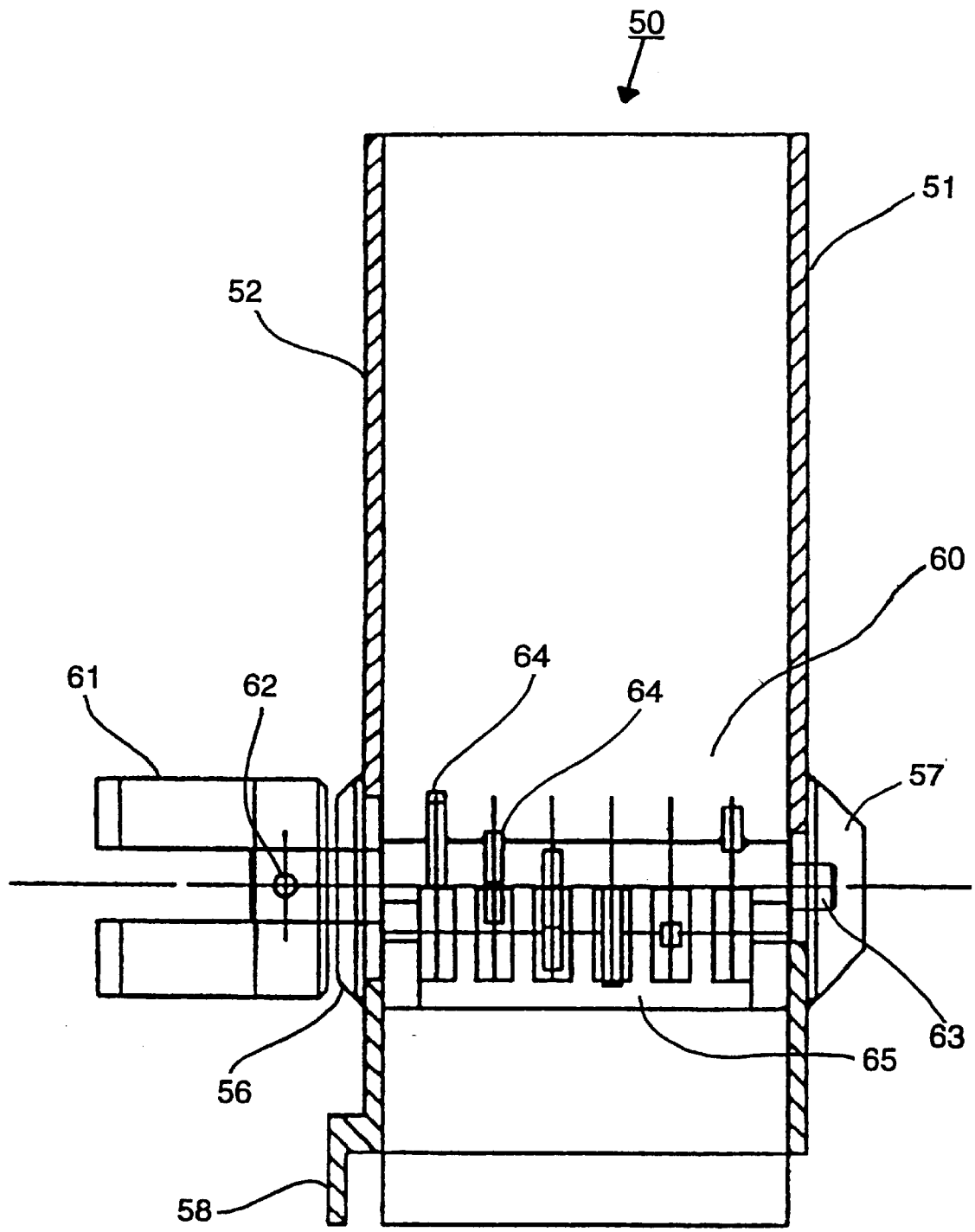
FIG. 6C is a section through the grinder assembly of FIG. 6A.

In FIG. 6C, there is shown a section A—A of FIG. 6B. This section shows a number of the elements described in FIGS. 6A and 6B. In addition, the grinder or cutter shaft 63 along with a plurality of grinder teeth 64 which mesh with the grate 65 are also shown. The grinder mechanism is described in further detail hereinbelow.

In FIG. 6D, there is shown a section of FIG. 6A, along line B—B, thus showing a top view of one embodiment of the grinder head. Evident are the cutter shaft 63, which emerges slightly from the front wall 51, and substantially from the rear wall 52. The shaft rides within bearings housed inside the front 57 and rear 56 endcaps. Also evident are the half grates 65a and 65b which are welded to the left 53 and right 54 chute side walls respectively. As can be seen, the cutter blades 64 are welded to the cutter shaft 63 in staggered positions about the shaft. Naturally, the blades may be welded to the shaft in other arrangements, but the staggered arrangement is preferred. Each blade 64 fits within a recess 65c in the left and right half grates 65a and 65b, each of which has a plurality of recesses 65c matching the number of cutter blades 64 welded to the cutter shaft 63. Accordingly, as bone to be ground is pressed down upon the rotating cutter assembly (the rotating cutting blades 64 welded to the rotating cutter shaft 63), the blades cut the bone as they pass upward and downward through the grate recesses 65c. Alternate embodiments of the grinder head vary the widths of the cutter blades 64 and the recesses 65c in the grate 65. In addition, the number (spacing) of the cutter blades 64 and thus grate recesses 65c, as well as the gaps between the front cutting edge of the tooth and the grating, may be varied between different embodiments of the grinder head to produce finer or coarser bone particle sizes. By appropriately matching the blades and grates, a series of grinder heads capable of producing bone particles of different sizes are achieved.

Figure 6E:
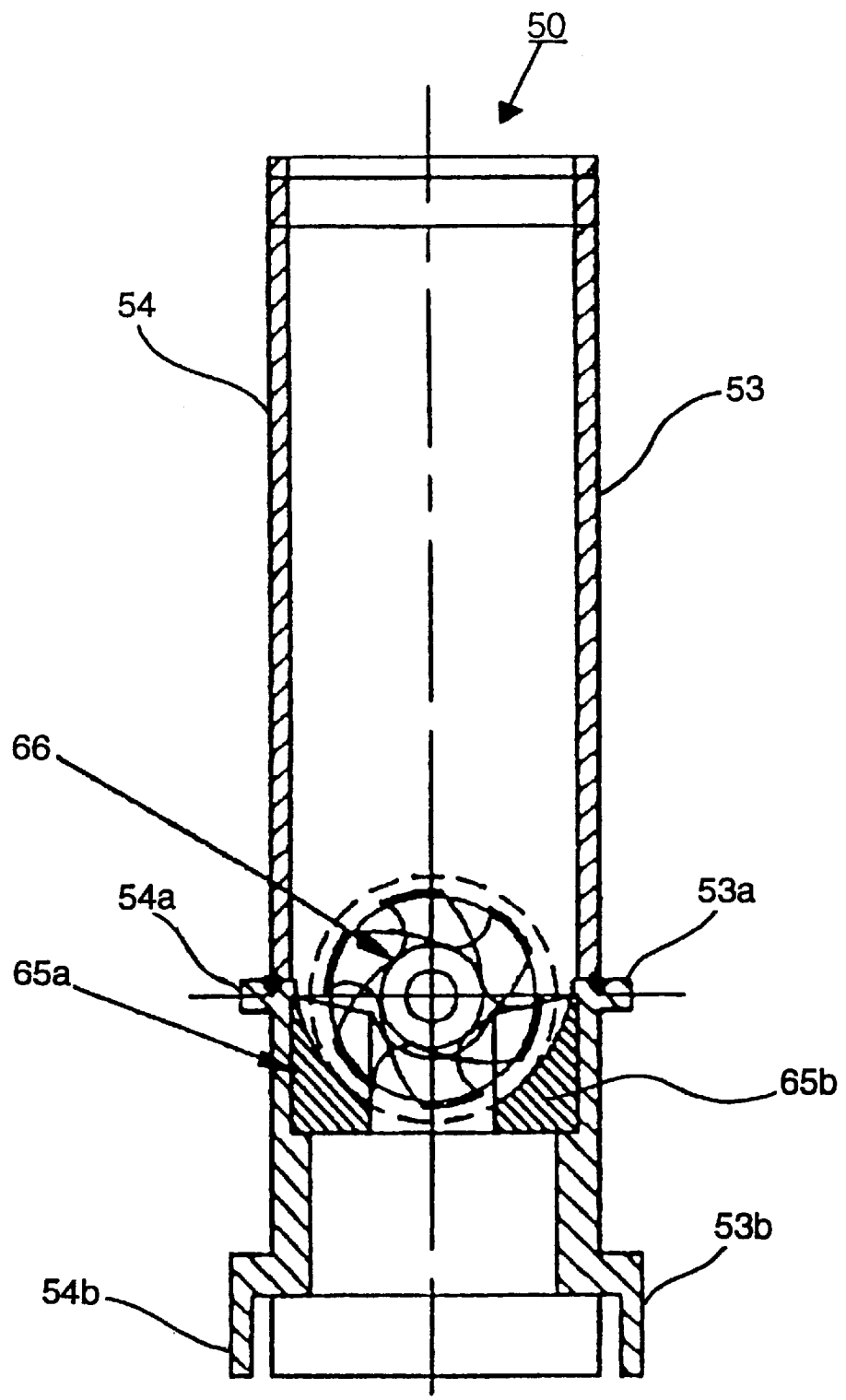
FIG. 6E is a section through the grinder assembly of FIG. 6A.

In FIG. 6E, there is shown a section of FIG. 6A along lines C—C. Like numbered elements are as described above. Also evident from this view are the side guide plates 53b and 54b respectively, a grinder head grate 65 and the cutter head assembly 66.

Figure 7A:
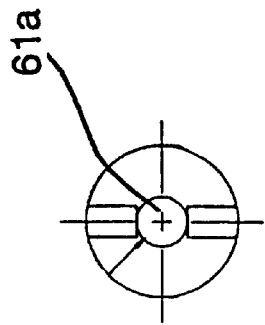
FIGS. 7A–7C are schematics of the motor drive shaft coupling.
Figure 7B:
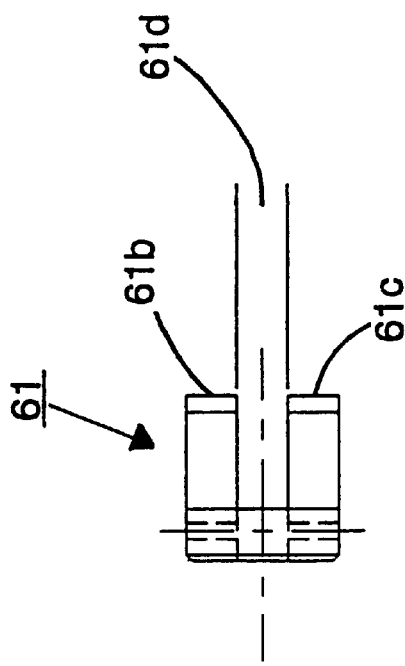
Figure 7C:
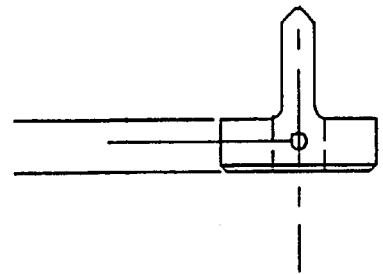
Figure 8C:
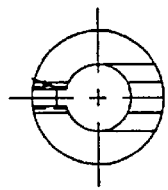
FIGS. 8A–8C are schematics of the grinder shaft coupling.
Figure 8B:
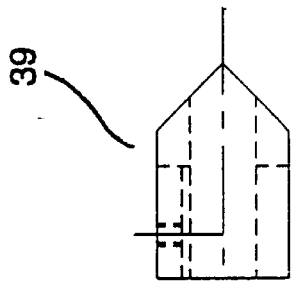
Figure 8A:
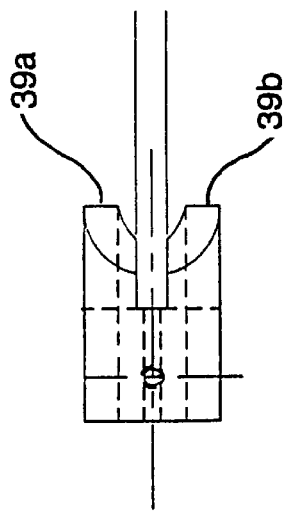

Referring now to FIG. 7, in a preferred embodiment, it can be seen that the motor drive shaft 38 is coupled to the cutter shaft 63 via novel couplings 39 and 61. A male coupler 61 has a center bore 61a of adequate diameter to accommodate the diameter of the cutter shaft 63, and is affixed thereto by a set screw, spring clip, or shear pin 62. The male coupler 61 has a pair of spaced-apart prongs 61b and 61c, with the spacing 61d therebetween being adequate to accommodate any forward projection on a female coupler 39. The tip of each prong 61b and 61c is preferably pointed. Alternatively, the male coupler may be a solid piece, with its front edge being wedge shaped. In FIG. 8, it can be seen that the female coupler 39 also preferably has a pointed pair of prongs 39a and 39b such that when the male and female couplings are brought into contact with each other, no matter what the orientation of each to the other is, the couplings properly seat with respect to each other to link the motor drive shaft 38 to the cutter shaft 63. Naturally, other couplings can be envisioned without departing from the principles of this invention. However, the novel design of the coupling disclosed here provides the advantage that a surgeon in the operating room is able to select any of a number of available chute 50 grinder head 60 assemblies and merely slide the assembly into the grinder, without giving a moment's thought to the alignment of the cutter 63 and motor drive 38 shafts.

Figure 9B:
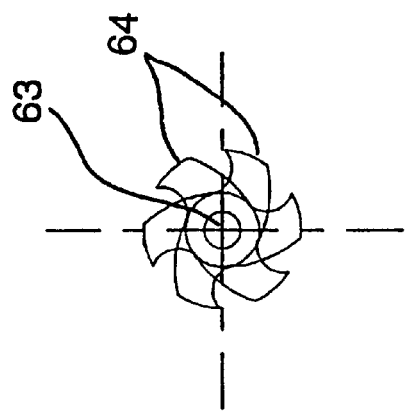
FIGS. 9A–9B are schematics of the cutter shaft.
Figure 9A:
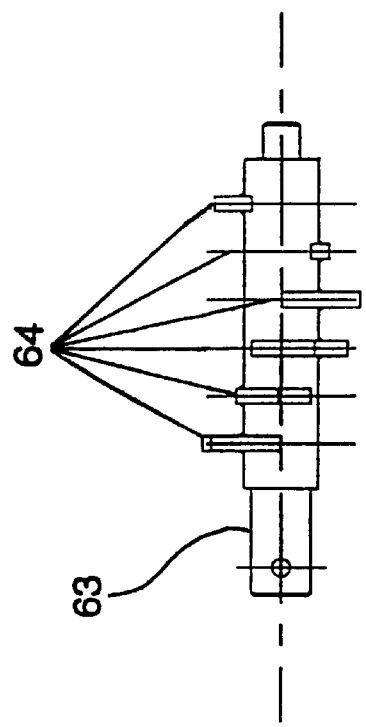

Referring now to FIG. 9, there is provided a detail of the cutter shaft 63. In FIG. 9A, in side view, the cutter shaft 63 is evident with the cutter blades 64 welded thereto in a staggered arrangement. Viewed down the axis of the cutter shaft 63, in FIG. 9B, the flower pattern of the welded blades 64 is evident. Naturally, variations on the shape of the cutter shaft 63 and the cutter blades 64 can be contemplated and used without departing from the spirit of this invention. However, the design of the cutter blades and shaft shown here are preferred.

Figure 10:
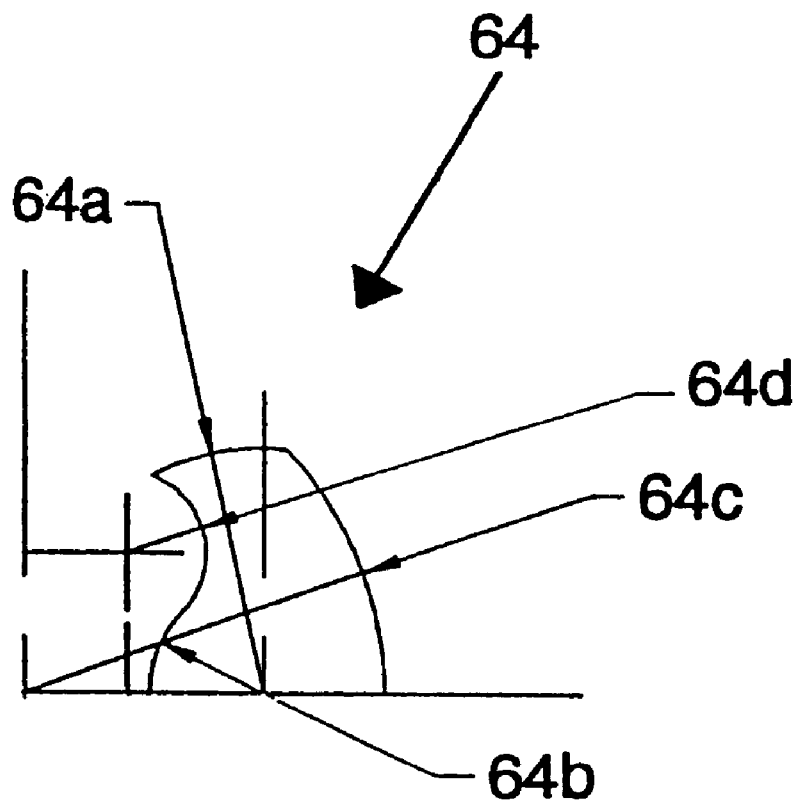
FIG. 10 is a schematic of the cutter blade.

In FIG. 10, a single cutter blade or cutter tooth 64 is depicted, with preferred dimensions shown. Thus, this embodiment displays a duckbill-shaped cutter tooth with a first radius 64a of about 0.66 inches, a second radius 64b of about 5/16 of an inch, a third radius 64c of about 0.97 inches, and a fourth radius 64d of about 7/32 inches. The tooth 64 is welded to the shaft, with either a groove being cut into the shaft or the tooth being welded thereto. It should be understood that these dimensions are provided only as an example and may be varied. It is the ratio of these dimensions to each other that is significant. Thus, as the absolute size of the cutter tooth is varied, it is preferred that these given dimensions are increased or decreased proportionally to maintain the appropriate ratios.

Referring to FIG. 11, there is provided several views of the receiver cup 70 of this invention. In FIG. 11A, there is provided a top view of the cup 70, showing the aspirator nipple 73 and safety rod 80. In FIG. 11B, there is provided a first section through line A—A. This view shows a screen ledge 74 on which a screen 71 may be placed. In FIG. 11C, there is shown a rear view of the cup 70 viewed down the axis of the safety rod 80. It will be appreciated that the receiver cup 70 and the safety interlock feature 80 need not be affixed to each other and this is only the case in one preferred embodiment of the invention.

In addition to the various parts of hardware that comprise the grinder, several disposable items are disclosed for use in combination with the device. Preferably, a kit is prepared which comprises at least the following items which are preferably factory packaged and sterilized together:

a. A sterile drape. The drape is used to isolate the grinder and head during any procedure including in the operating room or at a tissue bank, to maintain a sterile environment. The drape is preferably manufactured from a non-absorbent cloth material approximately 0.006 inches in thickness and about 52 inches by 48 inches in linear dimensions. The drape preferably has three rubber or like membrane openings which seal around the grinding head and safety interlock, thereby exposing only the parts which must be accessed by the user.

b. A receiver cup. The receiver cup is used as a receptacle for the ground bone particles and as a containment vessel for lavage. The cup preferably has dimensions of about 2 3/16 inch by 3 1/4 inches and about 2 inches in height. A safety interlock, i.e., the safety rod 80, also may be used as a handle for moving the cup containing ground bone without allowing contamination of the bone particles. When in operational position, the cup covers the bottom opening of the grinder head and eliminates access by the operator to the grinding teeth. The cup and a lid therefor may be made in a mold, preferably using polypropylene or like moldable material which has excellent radiation sterilization durability.

c. A mesh. The mesh is placed toward the bottom of the cup to allow cellular debris to be washed away during lavage while retaining the ground bone pieces. Preferably, the mesh is #304 stainless wire cloth or like material with rectangular openings and a wire diameter of about 0.035 inches. Preferably, the mesh has 10 meshes per inch (100 openings) which are desirably double crimp and weave welded.

d. Rubber tubing. Preferably, disposable Tygon tubing is used for water and debris vacuum exhaust from the receiving cup during lavage. One end of the tubing is attached to a spout 73 molded on the cup and the opposite end of the tubing is attached to a vacuum source.

In use, the grinder operates well in grinding cancellous and cortical bone, preferably from the metaphyseal and epiphyseal regions of the long bones, the ribs, iliac crests, vertebral bodies and like bones. While the grinder may be used with diaphyseal bone, this is not the primary bone stock intended for use with this device. The device may be used in an operating room setting or in a tissue bank setting for grinding of femoral heads (allograft or autografts), ribs, iliac crests, ilium and metaphyseal regions of long bones to produce cancellous or cortical-cancellous bone fragments for reconstructive purposes. The ground bone is then utilized in patients in need, for example, of total joint revisions, packing of bone defects, mal-union or non-union augmentation, multiple level spinal fusions (with or without instrumentation) and any other orthopaedic, maxillofacial, periodontal and neurosurgical procedures.

In a tissue bank setting, the bone grinder is used to produce allogeneic bone which is then packed and sold world-wide. The grinder is easily set up and there are no limitations on how much bone can be ground from available sources.

Due to the novel grinding heads of the bone grinder of this invention, the yield of useable ground bone particles is optimized. Most known bone grinding machines crush bone as they cut the bone, thereby yielding only about 60–70% useable bone of appropriate particle size. This is particularly disadvantageous where a patient's own bone (autologous bone) is used in the course of an operative procedure, as such bone source is naturally of very limited availability. The instant device is capable of producing 90% or greater useable bone of the desired particle size, thereby minimizing the wastage of bone from crushing.

From the foregoing description, it will be apparent that in use, a chute 50 housing an appropriate grinder head 60 is selected, slid into the housing 40, locked into position using lock pins 42a and 42b or like retention means, and attaching the receiver cup 70 to activate the motor. Bone is then fed into the top orifice of the chute 50 and ground by the grinder head 60. As the ground bone is delivered to the receiver cup 70 through the bottom orifice of the chute 50, the ground bone may be washed by either applying water, saline, alcohol or any other desired lavage fluid directly to the top of chute 50 or by removing the receiver cup and applying lavage with the cup removed from the grinder. By connecting an aspirator hose and a vacuum to the nipple 73, the lavage fluid and debris able to pass through the screen 71 is aspirated from the ground bone product. If ground bone particles of a different size are desired, the chute 50 housing the grinder head 60 is simply replaced with a different chute 50/grinder head 60 assembly bearing a cutter head capable of producing the desired bone particle size.

Having described in general and specific terms the components, manufacture and use of the grinder of this invention, it will be apparent that a novel bone grinder is disclosed herein which, in at least one embodiment, comprises a base plate to which is affixed a vertical wall that supports a forwardly projecting housing. A torque means is affixed to one side of the vertical wall with the forwardly projecting housing being affixed to the other side of the vertical wall. The drive shaft from the torque means is made to project through the vertical wall, with a coupling means affixed to the terminus of the drive shaft that projects through the vertical wall. A chute means, which is slidably affixable to the forwardly projecting housing, comprises a front wall, a rear wall, and two side walls, thereby defining a top receiving orifice and a bottom delivery orifice such that bone material may be delivered to the top orifice. Ground bone is delivered from bottom orifice as a grinder head is rotatably affixed within the chute, between the top orifice and the bottom orifice. Bone material delivered to the top orifice cannot traverse to the bottom orifice without contacting the grinder head.

It will also be appreciated that, according to this invention, control over the particle size and type of bone used for any given surgical procedure is obtained by interchanging the grinder head with any of a plurality of grinder heads having different numbers of cutting blades or different spacings between the cutting blades.

It will further be appreciated that, according to this invention, while the grinder head may be removable, it is preferred that the grinder head is rotatably fixed within the chute between the top orifice and the bottom orifice of the chute. In this manner, to interchange grinder heads, all that is required is for the entire chute assembly to be slid out of the device and a different chute slid into place.

It will be appreciated that, in operation, the cutter blades of the grinder head mesh and pass through a plurality of recesses in a grating against which the cutting blades can exert a force to cut bone pieces as the cutter blades pass into the grate recess.

While a plurality of different cutter blades known in the art could be used, in a preferred embodiment, the cutter blades have a first radius 64a of about 0.66 inches, a second radius 64b of about 5/16 of an inch, a third radius 64c of about 0.97 inches, and a fourth radius 64d of about 7/32 inches.

It will be appreciated that any of a number of couplings could be used to link the torque produced by a motor to a rotating cutter shaft. Per this invention, a preferred coupling comprises a linkage wherein the motor drive shaft is coupled to the cutter shaft via interlocking male and female couplers each of which have pointed edges so that when the male and female couplings are brought into contact with each other, no matter what the orientation of each to the other is, the couplings properly seat with respect to each other to link the motor drive shaft to the cutter shaft.

It will be appreciated that an optional but desirable feature of this invention is the provision of a safety interlock so that the motor cannot turn in the absence of proper placement of the safety interlock. In one embodiment of this invention, the safety interlock also acts as a receiving cup for ground bone as it is delivered from the bottom delivery orifice of the chute. The receiving cup may be separately sterilized, and is desirably a disposable surgical tray for receipt of ground bone. Furthermore, it is desirable for the receiving cup to house a mesh which prevents ground bone of a desired particle size from passing through the mesh but which permits debris of a smaller particle size to pass through. Provision of a vacuum connector to allow aspiration of lavage fluid used to wash ground bone particles retained on the mesh is also preferred.

It should be understood that the examples and embodiments described herein are for illustrative purposes only and that various modifications or changes in light thereof will be suggested to persons skilled in the art and are to be included within the spirit and purview of this application and the scope of the appended claims.

References

Weinmüller, Werner, German patent publication DE 3808409 (A1), published Sep. 28, 1989.
Setiey, Louis, Bruno Balay, Jean-Claude Cartillier, Claude Charlet, Alain Machenaud, Jean-Marc Semay, Jean-Pierre Vidalain, French patent publication 2712483, published May 24, 1995.
French patent publication 2199271, published Apr. 5, 1974.
Vermeulen, Eric, Gustave van Bogaert, U.S. Patent No. 4,252,282, issued Feb. 24, 1981.

We claim:

1. A bone grinder comprising:
    (a) a base plate;
    (b) a vertical wall affixed to said base plate;
    (c) a forwardly projecting housing affixed to said vertical wall;
    (d) a torque means affixed to said vertical wall on a side of said vertical wall opposite said forwardly projecting housing, with a drive shaft extending from said torque means through said vertical wall, said drive shaft having a drive shaft coupling means affixed to the terminus thereof which projects through said vertical wall;
    (e) a chute slidably affixable to said forwardly projecting housing, wherein said chute comprises a front wall, a rear wall, and two side walls, thereby defining a top receiving orifice and a bottom delivery orifice such that bone material may be delivered to the top orifice and delivered from said bottom orifice;
    (f) a grating structure affixed in said chute, said grating having a plurality of recesses; and
    (g) a grinder head assembly comprising:
        i. a cutter shaft;
        ii. a cutter shaft coupling means, said cutter shaft coupling means constructed and located on the cutter shaft so as to connect said cutter shaft to said drive shaft coupling means;
        iii. a plurality of cutter teeth or blades arranged in a spaced-apart and discontinuous manner on the exterior of a section of said cutter shaft positioned within said chute;
    wherein said cutter shaft is rotatably affixed within said chute, between said top orifice and said bottom orifice such that said torque means delivers torque through said drive shaft coupling means connected to said cutter shaft coupling means to rotate said cutter shaft, thereby causing said cutter teeth or blades to act on bone material introduced into said top orifice of said chute, and wherein said cutter teeth or blades mesh and pass through said plurality of recesses in said grating structure, thereby reducing the particle size of bone material introduced into said top orifice and made to contact said cutter teeth or blades.

2. The bone grinder of claim 1 wherein said grinder head assembly may be interchanged with alternate grinder head assemblies having different numbers of, different configurations of, or different spacings between said cutter teeth or blades.

3. The bone grinder of claim 1 wherein the cutter teeth or blades have a generally duckbill shape and first radius 64a of about 0.66 inches, a second radius 64b of about 5/16 of an inch, a third radius 64c of about 0.97 inches, and a fourth radius 64d of about 7/32 inches or dimensions of different absolute dimensions but similar ratios.

4. The bone grinder of claim 3 wherein said drive shaft extending from said torque means is coupled to the cutter shaft via drive shaft coupling means and cutter shaft coupling means that each have pointed edges so that when said couplings are brought into contact with each other, no matter what the initial orientation of each to the other is, the couplings rotate to properly seat with respect to each other to link the drive shaft extending from said torque means to the cutter shaft.

5. The bone grinder of claim 1 further comprising a safety interlock so that the motor cannot turn in the absence of proper placement of the safety interlock.

6. The bone grinder of claim 5 wherein a receiving cup is affixed to one or more components of the safety interlock, said receiving cup being positioned below said bottom orifice, such that said torque means can rotate only when the receiving cup affixed to said one or more safety interlock components is properly positioned in the bone grinder, and wherein the so positioned receiving cup receives ground bone that falls from the bottom orifice of the chute.

7. The bone grinder of claim 1 further comprising a receiving cup, wherein said receiving cup is a sterilized disposable cup adapted for receipt of ground bone.

8. The bone grinder of claim 7 wherein the receiving cup further comprises a mesh which prevents ground bone of a desired particle size from passing through the mesh but which permits debris of a smaller particle size to pass through.

9. The bone grinder of claim 8 wherein the receiving cup has a vacuum connector to allow aspiration of lavage fluid used to wash ground bone particles retained on the mesh.

10. The bone grinder of claim 1 wherein the torque means is an electrical motor, an air driven motor, or a hand crank.

11. A bone grinder comprising a torque means couplable to one of a plurality of interchangeable bone grinder heads to allow production of finer or coarser bone particles, depending on the bone grinder head used, each said bone grinder head comprising a front wall, a rear wall, and two side walls.

12. The bone grinder of claim 11 wherein ground bone particles produced by said grinder head are delivered to a receiver cup comprising a mesh and a vacuum aspirator nipple to allow lavage of retained ground bone particles in situ.

13. The bone grinder of claim 11, said bone grinder further comprising separately sterilizable kit components comprising a sterile drape, a receiver cup, a mesh, and a rubber tubing.

14. The bone grinder of claim 11 wherein the grinder head further comprises a rotating cutter shaft having a plurality of spaced-apart and discontinuous teeth or blades, and at least one stationary grating having recesses, whereby bone material is cut and reduced in size as the teeth or blades rotate through the recesses of said at least one stationary grating.

15. A snap-in unit for a bone grinder comprising a front wall, a rear wall, and two side walls, thereby defining a top receiving orifice and a bottom delivery orifice, said snap-in unit further comprising, interposed between said top orifice and said bottom delivery orifice, a means for grinding bone.

16. The snap-in unit of claim 15 further comprising, on the side walls of said unit, supports for sliding said snap-in unit into a bone grinder housing adapted for receiving the snap-in unit.

17. The snap-in unit of claim 15 wherein said means for grinding bone comprises a cutter shaft one end of which is rotatably positioned within said bone grinder head internal to said snap-in unit and the other end of which emerges from the rear wall of said snap-in unit.

18. The snap-in unit of claim 17 wherein the end of said cutter shaft that emerges from the rear wall of said snap-in unit has affixed to the terminal end thereof a coupling means.

19. The snap-in unit of claim 18 wherein said coupling means on the terminus of the cutter shaft comprises a coupling means with a pointed terminus that matably links to a complementary coupling means on the terminus of a torque means drive shaft which is also pointed along the mating end of the coupling and which is adapted to mate with the coupling on the terminus of the cutter shaft such that no matter what the initial orientation with respect to each other of said coupling means on either the cutter or torque means drive shaft, upon contact with each other, the two coupling means slide along each other to seat properly.

20. The snap-in unit of claim 19 wherein the unit, when snapped into the bone grinder, is retained in place by a pair of easily insertable lock pins.

21. The snap-in unit of claim 20 wherein the cutter shaft has a plurality of cutter teeth or blades affixed thereto wherein said cutter teeth or blades have a hook-bill shape.

22. The snap-in unit of claim 21 wherein the cutter blades or teeth are affixed to the cutter shaft in a staggered arrangement.

23. The snap-in unit for a bone grinder, according to claim 15, wherein said means for grinding bone comprises a rotatable cutter shaft having a plurality of spaced-apart and discontinuous teeth or blades, and at least one stationary grating having recesses, whereby bone material is cut and reduced in size as the teeth or blades rotate through the recesses of said at least one grating.

24. A modular bone grinder comprising:
  (a) a grinder head comprising a cutter shaft, a plurality of spaced-apart and discontinuous cutter teeth or blades and a cutter shaft coupling, said grinder head being easily removed and separately sterilized from the remainder of the grinder and which can be easily reinserted into the bone grinder;
  (b) a torque means comprising a drive shaft and a drive shaft coupling for exerting torque on the coupled cutter shaft when the grinder head is inserted into the bone grinder; and
  (c) a receiver cup which can be separately sterilized from the remainder of the elements of the bone grinder;
wherein said cutter shaft coupling mates with said drive shaft coupling without the need for manual alignment of said couplings and wherein said torque means causes the cutter shaft to rotate and cut bone introduced into the grinder head to form bone particles and wherein said bone particles so produced fall into said receiving cup removably situated below said grinder head.

25. A method for grinding bone removed from a patient in the course of surgery which comprises:
  (a) removing a portion of the patient's bone to be ground;
  (b) grinding said portion of the patient's bone in a sterile, modular bone grinder comprising a torque means and a bone grinder head that is interchangeable to allow production of ground bone in the form of finer or coarser bone particles, depending on the bone grinder head used,
wherein each said bone grinder head has a top orifice for adding bone and a bottom orifice for dispensing ground bone; and
  (c) collecting the patient's ground bone in a sterile receiver cup situated beneath the bottom orifice of said bone grinder head.

26. The method of claim 25 further comprising retaining, on a mesh located in said receiver cup, bone ground to a particular size, upon release of ground bone into said receiver cup, said mesh selected to permit removal of particles smaller than the desired ground bone particle size retained on said mesh.

27. A bone grinder comprising a torque means couplable to one of a plurality of interchangeable bone grinder heads to allow production of finer or coarser bone particles, depending on the bone grinder head used, each said bone grinder head comprising a front wall, a rear wall and two side walls, wherein each said interchangeable bone grinder head further comprises:

(a) a chute comprising four connected walls defining a top orifice and a bottom orifice such that bone material may be delivered to the top orifice for delivery from the bottom orifice;

(b) a space below said bottom orifice for accommodating a receiving cup; and (c) a grinder head assembly positioned between said top and bottom orifices, comprising a cutter shaft, a cutter shaft coupling means so constructed and located on said cutter shaft as to connect said cutter shaft to said torque means, a plurality of cutter teeth or blades arranged in a spaced-apart and discontinuous manner on the exterior of a section of said cutter shaft disposed within said chute, said grinder head assembly being removably affixed within said chute; wherein said torque means delivers torque through said cutter shaft coupling means to rotate said cutter shaft, causing said cutter teeth or blades to act on bone material introduced into said top orifice of said chute, whereby said cutter teeth or blades exert a force to reduce the particle size of contacted bone material.

* * * * *